United States Patent [19]

Briggs

[11] Patent Number: 4,585,883
[45] Date of Patent: Apr. 29, 1986

[54] PREPARATION OF ORGANOMETALATES

[75] Inventor: John R. Briggs, Charleston, W. Va.

[73] Assignee: Union Carbide Corporation, Danbury, Conn.

[21] Appl. No.: 594,389

[22] Filed: Mar. 28, 1984

[51] Int. Cl.$^4$ ............................ C07F 9/00; C07F 11/00
[52] U.S. Cl. ............................................ 556/42; 556/57
[58] Field of Search ...................... 260/429 R; 556/42

[56] References Cited

U.S. PATENT DOCUMENTS

| | | | |
|---|---|---|---|
| 2,909,541 | 10/1959 | Hugel | 260/429 R |
| 2,938,869 | 5/1960 | Hugel | 260/429 R X |
| 3,223,625 | 12/1965 | Cyphers et al. | 260/429 R X |
| 3,956,180 | 5/1976 | Cavitt . | |
| 4,217,292 | 8/1980 | Kroenke . | |
| 4,225,484 | 9/1980 | Kroenke | 260/429 R X |
| 4,343,746 | 8/1982 | Anglin et al. | 260/429 R |
| 4,343,747 | 8/1982 | Ryu et al. | 260/429 R |
| 4,406,837 | 9/1983 | Kroenke . | |
| 4,406,838 | 9/1983 | Kroenke . | |
| 4,406,839 | 9/1983 | Kroenke et al. . | |
| 4,406,840 | 9/1983 | Kroenke . | |
| 4,410,462 | 10/1983 | Kroenke | 260/429 R |
| 4,410,463 | 10/1983 | Kroenke | 260/429 R |
| 4,412,956 | 11/1983 | Abramson et al. . | |
| 4,424,164 | 1/1984 | Kroenke | 260/429 R |
| 4,425,279 | 1/1984 | Kroenke | 260/429 R |

OTHER PUBLICATIONS

A. Martinsen, "Preparation and Properties of Some Bis(triphenylphophine)iminium Salts", [(PH$_3$P)$_2$N]X, Acta Chemica Scandinavica, A31 (1977), No. 8, pp. 645–650.
Inorganic Syntheses, vol. 15, pp. 84–90.

Primary Examiner—Helen M. S. Sneed
Attorney, Agent, or Firm—D. T. Trinker

[57] ABSTRACT

Organometalates are prepared by the reaction, in a liquid reaction menstruum, between a soluble salt of an organic-containing cation and a heavy metal salt, e.g., silver salt, of a metalate to produce a soluble organometalate and a substantially insoluble heavy metal salt. The heavy metal salt of the metalate may be substantially insoluble in the reaction menstruum. The organometalates are useful to enhance the selectivity to monoalkylene glycols when provided in processes for the hydrolysis of alkylene oxides.

30 Claims, No Drawings

PREPARATION OF ORGANOMETALATES

This invention relates to the preparation of compounds having an organic-containing cation and a metalate anion. The processes of this invention involve reacting, in a solution, a dissolved organo salt with a heavy metal metalate wherein the heavy metal-containing reaction product is a solid in the reaction medium. Often, the processes can be conducted relatively rapidly with high yields to the desired organometalates even at relatively low temperatures.

Various organometalates have been disclosed. For instance, Kroenke, in U.S. Pat. No. 4,217,292, issued Aug. 12, 1980, describes amine molybdates prepared by reacting molybdenum trioxide with an amine in an aqueous medium that is essentially free of acid and contains a water-soluble ammonium and/or metal salt of an acid. More recently Kroenke, in U.S. Pat. Nos. 4,406,837; 4,406,838; 4,406,839; and 4,406,840, all issued on Sept. 27, 1983, disclosed organic-containing ammonium and amine molybdates. In U.S. Pat. No. 4,406,837, methyltricaprylammonium molybdates are prepared by reacting ammonium dimolybdate with methyltricaprylammonium chloride in an acidic aqueous medium. In U.S. Pat. No. 4,406,838, trioctylammonium molybdates are prepared by reacting ammonium dimolybdate with trioctyl amine in an acidic aqueous medium. In U.S. Pat. No. 4,406,840, tri(tridecyl)ammonium molybdates are prepared by reacting ammonium dimolybdate with tri(tridecyl)amine in an acidic aqueous medium. A process for preparing amine molybdates is disclosed in U.S. Pat. No. 4,406,839 in which a two liquid phase reaction mixture is employed. A molybdenum reactant (such as molybdenum trioxide, molybdic acid or salt) is provided in solution in an aqueous phase, and an amine or amine salt reactant (such as primary, secondary or tertiary amines or quarternary ammonium salts) is or becomes dissolved in an immiscible organic phase. The amine molybdate is dissolved in the organic phase. An inorganic acid is preferably added to the reaction mixture.

Abramson, et al., in U.S. Pat. No. 4,412,956, issued Nov. 1, 1983, disclose a process for making alkyl vanadates by reacting vanadium pentoxide with an alkyl alcohol in the presence of a basic nitrogenous compound which is described as a catalyst. The basic nitrogenous compounds disclosed include ammonia and ammonium compounds, amines, formamide compounds, urea, pyridine, guanidine carbonate and the like.

A. Martinsen, et al., in "Preparation and Properties of Some Bis(triphenylphosphine)iminium Salts, [(Ph$_3$P)$_2$N]X", *Acta Chemica Scandinavica*, A 31 (1977) No. 8, pages 645 to 650, describe the preparation of bis(triphenylphosphine)iminium salts by precipitation from a warm, aqueous reaction medium employing the corresponding chloride salt and an alkali metal salt of the desired anion. Various anions disclosed by the authors include chromate, sulfate, nitrate and nitrite. The authors note that the fluoride cannot be prepared from the chloride and excess potassium fluoride. They do disclose that the fluoride can be prepared from the iodide and silver fluoride in methanol.

The compounds previously disclosed have been attributed to have various utilities. For example, the molybdates disclosed by Kroenke are described as smoke retardant additives for vinyl chloride polymer compositions. Recently, various metalates have been proposed for enhancing the selectivity of the hydrolysis of alkylene oxides to monoalkylene glycols.

U.S. patent applications Ser. Nos. 428,815, filed Sept. 30, 1982, (now abandoned) and 530,235, filed Sept. 8, 1983, of J. H. Robson and G. E. Keller, disclose the production of monoalkylene glycols with high selectivity by the reaction of a vicinal alkylene oxide with water in the presence of a water-soluble metavanadate. Hence, lower water to alkylene oxide ratios can be employed using the disclosed process with attractive selectivities to the monoglycol products. The counter ion to the metavanadate is selected to provide a water-soluble metavanadate salt under the reaction conditions employed and alkali metals, alkaline earth metals, quaternary ammonium, ammonium, copper, zinc, and iron are suggested cations. It is also disclosed that the metavanadate may be introduced into the reaction system in the salt form or on a support such as silica, alumina, zeolites and clay.

In copending U.S. patent application Ser. No. 594,264, of J. R. Briggs and John H. Robson, filed on even date herewith, various vicinal dioxyalkylene organometalates are disclosed which are useful in making alkylene glycols when contacted with water. Copending U.S. patent application Ser. No. 594,256, filed on even date herewith, of J. R. Briggs, G. L. O'Connor and J. H. Robson, discloses, among other things, the use of organometalates in processes for making alkylene glycols from alkylene oxides wherein the organometalate is first contacted with the alkylene oxide in the substantial absence of water, and then contacted with water to form the alkylene glycol with a high yield of the monoalkylene glycol. In an aspect of that invention the organometalate can be readily recovered from the reaction medium by phase separation or selective extraction into an immiscible organic phase.

Another process involving the use of organometalates is disclosed in U.S. patent application Ser. No. 594,385, filed on even date herewith, of J. R. Briggs and J. H. Robson, wherein a two-phase reaction zone is maintained for the hydrolysis reaction. The organometalate is preferentially soluble in an organic phase (such as toluene or dischloromethane). The organometalate can be recovered by separation of the organic phase, and the organic phase, which contains the organometalate, can be returned to the reaction zone.

U.S. patent applications Ser. Nos. 530,235; 594,264; 594,256; and 594,385 are herein incorporated by reference.

The viability of these processes, is, in part, dependent upon the ability to make the organometalates. Commercially-available metalates, such as alkali metal molybdates, tungstates and vanadates, are advantageously converted to organometalates having desirable solubility parameters in both aqueous and organic media in order that the organometalate is sufficiently preferentially soluble in a water-immiscible organic phase that little organometalate is lost from a hydrolysis process. Accordingly, processes to prepare organometalates should be versatile to provide ample freedom to make the organocations of varying organophilicity. Moreover, the process should enable readily available and relatively inexpensive raw materials to be employed. Further, the process should not be capital or energy intensive, and should enable the organometalate product to be recovered easily and in high purity.

SUMMARY OF THE INVENTION

In accordance with this invention, heavy metal salt of the metalate is reacted in solvent-containing menstruum with a salt of the organo-containing cation which is soluble in the reaction menstruum. The organic-containing solvent is capable of dissolving the organometalate product while the heavy salt by-product is substantially insoluble. The heavy metal salt by-product can be removed by decanting the liquid phase or by filtration, and the organometalate can then be recovered from the liquid phase by, for example, evaporation of the solvent. Thus, the processes of this invention enable the facile production of a wide variety of organometalates.

DESCRIPTION OF PROCESS

The processes of this invention involve the formation of a solid heavy metal salt by-product in the reaction medium. Thus, the selections of the solvent and starting reactants are important considerations. Frequently, the heavy metal and the counter-ion to the organic-containing cation are selected such that the organic-containing cation metalate salt is soluble in the organic-containing menstruum under the reaction conditions but a relatively insoluble by-product salt is formed. Heavy metal cations include calcium, barium, lead, bismuth, lanthanum and silver. Because silver forms insoluble salts with many anions, it is often selected as the heavy metal cation. The counter-ion to the organic-containing cation is selected in combination with the heavy metal cation. Thus, while many anions may find application, e.g., halides such as chloride, bromide and iodide; sulfate; silicate; carbonate; etc., not all anions will be useful with all heavy metal cations. Because of the ready formation of insoluble salts, halides are frequently employed as anions especially when silver is the heavy metal cation.

The solvent-containing menstruum is capable of dissolving the organic-containing cation salt reactant and the organometalate under the reaction conditions. The heavy metal metalate reactant need not be dissolved under the conditions of the reaction; however, in some instances, it may be dissolved. Generally, the solubility of the heavy metal salt by-product in the menstruum is less than about 0.1 gram per liter at 25° C., and often the solubility is less than 0.001 gram per liter at 25° C.

The menstruum can contain water as the solvent but often comprises an organic solvent, say, about 5 to 100, preferably, about 50 to 100, and in most instances about 90 to 100, volume percent of the organic-containing menstruum is organic solvent. Organic solvents include solvents which are liquid under the reaction conditions and relatively inert. Solvents which are capable of complexing with metal cations such as some of the cryptands, carboxylic acids and esters, are often not employed since the solubility of the heavy metal salt by-product may be undesirably high.

Typical solvents include aromatic hydrocarbons such as benzene, xylene, toluene, cumene, naphthene, chlorobenzene, etc.; alkanes such as iso-pentane, n-pentane, dichloromethane, 1,1,2-trichloroethane, carbon tetrachloride; ethers such as diethyl ether, methoxyethanol, etc.; amides; ketones, such as acetone, dimethyl ketone, methyl ethyl ketone, etc.; phosphine oxides; sulfoxides, such as dimethylsulfoxide, diethylsulfoxide and the like.

The amount of reactants employed generally depends on their solubility in the reaction menstruum and the solubility of the organometalate in the reaction menstruum. In many instances, each reactant is provided in an amount of about 1 to 500, say, 10 to 200, grams per liter of the reaction menstruum. The mole ratio of the heavy metal metalate to the organic-containing cation salt can vary widely, for instance, from about 100:1 to 1:100. Most often, however, the ratio is close to that required on a stoichiometric basis for the reaction to produce the organometalate, e.g., the ratio is about 20:1 to 1:2, say, about 10:1 to 1:1.5.

Desirably, to ensure substantially complete conversion the mole ratio of the heavy metal metalate to the organic-containing cation is greater than one times the amount required on a stoichiometric basis for the desired reaction. Additionally, when complete conversion of the organic-containing cation salt is sought, the medium may be subjected to one or more contactings with heavy metal metalate provided in a substantial excess for reaction with the remaining organic-containing salt. With, for example, organomolybdate and organotungstates, two cation sites exist. Hence, the mole ratio of organic-containing cation salt to metalate salt should be greater than 1:1 when the bis(organo)metalate is sought and less than 2:1 when mono(organo)metalate is sought.

When the heavy metal metalate is substantially insoluble in the reaction menstruum, it is preferred that it is employed in stoichiometric excess such that the reaction menstruum at the conclusion of the reaction will have a minimum amount of unreacted organic-containing cation salt. Advantageously, such solid, heavy metal metalate is of a relatively fine particle size, when introduced into the reaction menstruum, e.g., it has a major dimension of less than about 100 microns, say, less than about 40 microns, often in the range of about 0.1 to 20 microns.

In many instances, ambient temperature (e.g., 18° C. to 25° C.) is adequate for the process; however, higher or lower temperatures can be employed. Generally, the temperature is between from about $-10°$ C. to 150° C. or more, frequently about 10° C. to 70° C. Typically, there is little advantage in using substantially elevated or substantially reduced reaction pressures. The selection of the pressure is often determined on the basis of processing convenience and thus frequently ranges from about 0.75 to 5 kg/cm absolute.

The recovery of the organometalate can be effected by any suitable means. Generally, the solid heavy metal salt by-product is removed by centrifuging, decanting and/or filtration. Often a flocculant or filter aid is used to assist in the separation of the solids. The remaining liquid may then be distilled or evaporated to leave the organometalate product or it may be chilled to sufficiently reduce the solubility of the organometalate that at least a portion precipitates and can be recovered by a solid-liquid separation such as centrifuging, decanting and/or filtration. Alternatively, the solution may be used in the hydrolysis of alkylene oxide.

THE PREPARATION OF HEAVY METAL METALATES

Commercially-available metalates are often alkali metal metalates, ammonium metalates or acids such as sodium molybdate, potassium molybdate, molybdic acid, sodium metavanadate, sodium orthovanadate, potassium vanadate, ammonium metavanadate, vanadium pentoxide, sodium tungstate, and the like. Therefore, it is often desirable to convert these commercially-available metalate salts and acids into heavy metal metalates. While many procedures can be employed, a particularly convenient process is to admix soluble metalates with water-soluble heavy metal salts in a solution in which the heavy metal metalate is insoluble. For instance, sodium molybdate and silver nitrate can be admixed in water. The silver molybdate precipitates and can be recovered by, for example, filtration.

DESCRIPTION OF ORGANOMETALATES

The organometalates made in accordance with the processes of this invention may be represented by the formula:

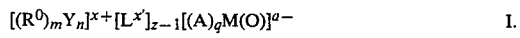
$$[(R^0)_m Y_n]^{x+}[L^{x'}]_{z-1}[(A)_q M(O)]^{a-} \qquad \text{I.}$$

wherein $[(R^0)_m Y_n]^{x+}$ is an organic-containing cation having a positive charge of x, in which organic-containing cation Y is a polyvalent element which is an ionic charge carrying center, $R^0$ is hydrogen or hydrocarbyl-containing substituent with the proviso that the organic-containing cation has at least one $R^0$ which contains a hydrocarbyl substituent, m is the average number of electron pairs shared by each Y with the $R^0$ groups, n is the number of charge carrying centers, wherein m, n and x are related by the equation $x=n(V-m)$ in which V is the average functional oxidation state of each Y wherein each electron pair used by each Y in bonding to $R^0$ is given the value of 1 and the functional oxidation state of Y is the sum of the electron pairs bonding to $R^0$ and x/n, wherein x is an integer of 1 or 2; wherein L is a cation which has a positive charge of x' and which may be the same or different from the organic-containing cation, where x' is usually an integer of 1 or 2; wherein z is the number of cations which is usually from 1 to 3; and wherein

$$[(A)_q M(O)]^{a-} \qquad \text{II.}$$

is a metalate anion having a negative charge of a, in which a equals the amount of $x+[(z-1)(x')]$ and is usually between $-1$ and $-4$; M is a polyvalent metal having a functional positive oxidation state of w wherein the absolute value of w equals the absolute value of $(q+2)$ and w is usually $+3$ to $+6$ or $+7$, A is a substituent to fill the remaining valencies (q) of M.

The hydrocarbyl-containing substituents useful in the organic-containing cation contain at least one carbon atom, frequently at least four carbon atoms, and may be further substituted with moieties that are not reactive with the anion. L may be any suitable cation and often is another organic-containing cation or a non-organic-containing cation such as an alkali or alkaline earth metal or an ammonium or phosphonium cation, and serves to balance the charge of the anion. The metalate anions of the organometalates are characterized by an anionic structure containing at least one metal atom and at least one oxygen ligand conventionally characterized as double-bonded oxygen atom.

The substituents, A, to fill the remaining valencies (q) of M may be the same or different and may be, for instance, double-bonded oxygen or sulfur; an organic radical such as an alkyl, alkoxy, acyl, aryl, amino, phosphino, etc., usually of 1 to about 12 carbon atoms; halogen (e.g., chlorine, fluorine, iodine); —O— or —S— wherein the remaining valency of the oxygen atom is in free ionic form or is bonded to metal atom (as in a bimetal or polymetal-containing metalate) or cation. Most commonly, A is —O— or =O.

Particularly preferred metals for metalate anions include the metals in groups Vb and VIb of the periodic chart such as vanadium, molybdenum and tungsten, athough other metals such as rhenium and germanium may also find application. Particularly desirable metalates are those which demonstrate significant selectivity-enhancement to monoalkylene glycols during the hydrolysis of the corresponding alkylene oxide. Representative of these desirable metalate anions are molybdate, tungstate, metavanadate, hydrogen pyrovanadate and pyrovanadate; although because of the complex chemistry associated with many metalates, especially the vanadates, the precise structure of the selectivity enhancing specie or species may be different.

Not all metalates, including those of vanadium, tungsten and molybdenum, exhibit desired selectivity-enhancing properties. For example, paramolybdate and paratungstate anions (as the metalate anion added) appear to exhibit little, if any, of this activity. Orthovanadate anions (as that species) in the presence of water promote reactions between alkylene oxide and alkylene glycol through base catalysis with little selectivity improvement being observed. It is, however, frequently possible to chemically alter the metalate to form a species believed to be active. For instance, orthovanadate may be converted to a selectivity-enhancing species by pH adjustment.

In an aspect of the invention, the metal for the metalate is selected on the basis of the nucleophilicity and electrophilicity in the anion with respect to alkylene oxide in the environment. For example, the metal as in the metalate often has a nucleophilicity with respect to ethylene oxide greater than that exhibited by rhenium as in rhenate anion under the same conditions. Also, it is frequently the case that the metal as the metalate has an electrophilicity with respect to ethylene oxide greater than that exhibited by vanadium in orthovanadate (as that species) under the same conditions.

A particularly convenient method for approximating nucleophilicity and electrophilicity characteristics of a metal in a metalate anion is by comparing the rate and selectivity to monoethylene glycol under substantially the same hydrolysis conditions but employing an equimolar amount (based on the anion) of the subject metalate anion and the reference anion. For the sake of ease in ascertaining the nucleophilicity and electrophilicity of metal in a metalate anion, the cation may be sodium. If the rate and/or selectivity to the monoethylene glycol is greater than that provided by the rhenate anion, then the metal as the metalate is probably more nucleophilic than rhenate with respect to ethylene oxide. If the production of diethylene glycol and polyethylene glycol is greater than that provided with orthovanadate, regardless of the rate of formation of ethylene glycols, then the metal as the metalate is probably less electrophilic than orthovanadate with respect to ethylene oxide.

The organic-containing cation of the organometalate is characterized as having a polyvalent element, Y. Polyvalent elements include the elements in Groups Va and VIa of the periodic chart, such as nitrogen, phosphorus, arsenic, antimony, and sulfur. Advantageously, the cation is stable in the presence of water. Hence, Y is preferably not oxygen. From the standpoints of stability and availability, Y is usually phosphorus, sulfur and, especially, nitrogen.

It is often desirable that the cation has a marked solubility in an organic medium and is preferentially soluble in the organic medium as compared to water. Frequently, the hydrocarbyl-containing compound of the cation is sufficient to impart a greater solubility of the organometalate in a given water-immiscible organic solvent, such as toluene, than in distilled water at a given temperature, say, 25° C. In some instances, the solubility coefficient is at least 5 times, say, at least 20 times, greater in toluene than the solubility coefficient of the organometalate in distilled water at 25° C. In some instances, the organometalate may be one which is substantially insoluble in distilled water, e.g., less than about 50, say, less than about 10, grams of the organometalate will dissolve in a liter of distilled water at 25° C. Some organometalates are immiscible with distilled water and some are solid at ambient temperatures, for instance, 25° C., or even at temperatures suitable for alkylene oxide hydrolysis, e.g., about 50° to 250° C.

Since the hydrophilicity and organophilicity of the organometalates are influenced by the hydrocarbyl content of the organic-containing cation, it frequently contains at least one substituent having at least four carbon atoms. No theoretical maximum exists for the total number of carbon atoms in any one substituent on Y or in the total substituents on Y.

In one aspect of the invention, Y is a polyvalent element in group Va of the periodic chart, e.g., ammoniums, phosphoniums and arsoniums and some of the cation structures may be represented by the formula.

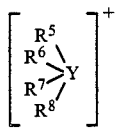

and for members of group VIa of the periodic chart, e.g., sulfoniums, by the formula

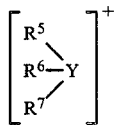

Each of $R^5$, $R^6$, $R^7$ and $R^8$ may be the same or different and may combine to form cyclic structures. Exemplary of each of $R^5$, $R^6$, $R^7$ and $R^8$ are hydrogen and hydrocarbyls which may be substituted or unsubstituted and contain at least 1 carbon atom and, preferably, at least one, and most preferably all, contain at least about 4 carbon atoms, e.g., about 4 to 70, and sometimes 4 to 20, carbon atoms. However, at least one of the substituents must be hydrocarbyl-containing.

The hydrocarbyl substituents may be aliphatic or aromatic and include, for example, n-hexyl, cyclohexyl, phenyl, benzyl, naphthyl, and the like. Illustrative of the quaternary ammonium and quaternary phosphonium moieties are tetrahydrocarbyl ammoniums, e.g., tetramethyl ammonium, tetraethyl ammonium, tetra-n-propyl ammonium, tetra-n-butyl ammonium, tetra-isobutyl ammonium, trimethyl butyl ammonium, tetraheptyl ammonium, tetraphenyl ammonium, tetrabenzyl ammonium, tetradodecyl ammonium, tetraoctadecyl ammonium, and the like; trihydrocarbyl ammonium, e.g., trimethyl ammonium, triethyl ammonium, triphenyl ammonium, tridodecyl ammonium, trioctadecyl ammonium, and the like; dihydrocarbyl ammoniums, e.g., dimethyl ammonium, diethyl ammonium, di-n-butyl ammonium, di-n-heptyl ammonium, diphenyl ammonium, dibenzyl ammonium, didodecyl ammonium, dioctadecyl ammonium, and the like; hydrocarbyl ammoniums, e.g., methyl ammonium, n-butyl ammonium, dodecyl ammonium, octadecyl ammonium, phenyl ammonium, benzyl ammonium, and the like; tetrahydrocarbyl phosphoniums, e.g., tetramethyl phosphonium, tetraethyl phosphonium, tetra-n-propyl phosphonium, tetra-n-butyl phosphonium, tetra-isobutyl phosphonium, trimethyl butyl phosphonium, tetraheptyl phosphonium, tetraphenyl phosphonium, tetrabenzyl phosphonium, tetradodecyl phosphonium, tetraoctadecyl phosphonium, and the like; trihydrocarbyl phosphonium, e.g., trimethyl phosphonium, triethyl phosphonium, triphenyl phosphonium, tridodecyl phosphonium, trioctadecyl phosphonium, and the like; dihydrocarbyl phosphoniums, e.g., dimethyl phosphonium, diethyl phosphonium, di-n-butyl phosphonium, di-n-heptyl phosphonium, diphenyl phosphonium, dibenzyl phosphonium, didodecyl phosphonium, dioctadecyl phosphonium, and the like; hydrocarbyl phosphoniums, e.g., methyl phosphonium, n-butyl phosphonium, dodecyl phosphonium, octadecyl phosphonium; phenyl phosphonium, benzyl phosphonium, and the like.

Another group of organic-containing cations includes the bis(hydrocarbyl-phosphine)iminiums represented by the formula:

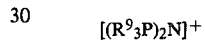

wherein each $R^9$ may be the same or different and may be the same as set forth for $R^5$ to $R^8$. Illustrative of bis(hydrocarbylphosphine)iminiums are bis(triphenylphosphine)iminium, bis(tribenzylphosphine)iminium, bis(trimethylphosphine)iminium, bis(tridodecylphosphine)iminium, and the like.

A further group of organic-containing cations have the formula:

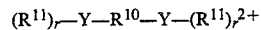

wherein $R^{10}$ is alkylene of 1 to about 6 carbon atoms, $R^{11}$ is hydrogen or hydrocarbyl which may be substituted or unsubstituted and r is 3, such as the quaternized diamines, quaternized diphosphines, etc. Members of this group include
N,N'-bis(trimethyl)propylene diamine,
N,N'-bis(triphenyl)propylene diamine,
N,N'-bis(trioctadecyl)propylene diamine,
P,P'-bis(trimethyl)propylene diphosphine, and the like.

The anion of the organometalate may be associated with cations in addition to the organic-containing cation. These cations, i.e., L of Formula I, may include alkali metals, alkaline earth metals, copper, zinc, iron, ammonium cations, phosphonium cations, sulfonium cations, and other cations including organic-containing cations, e.g., containing alkyl, alkoxy, acyl, aryl, amino, phosphino, etc., groups of 1 to about 12 carbons.

DISCUSSION OF ALKYLENE GLYCOL FORMATION

Alkylene oxides which may be used to produce alkylene glycols using organometalates have the general formula:

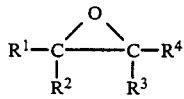

wherein $R^1$, $R^2$, $R^3$ and $R^4$ are the same or different and are hydrogen or hydrocarbyl-containing substituents of 1 to about 20 carbon atoms. Often $R^1$, $R^2$, $R^3$ and $R^4$ are the same or different and are hydrogen, alkyl of between 1 and about 10 carbons, monocyclic or bicyclic aryl having up to about 12 carbons, alkaryl having 7 to about 10 carbons, monocyclic or bicyclic aralkyl having 7 to about 15 carbons, alkenyl having 2 to 3 carbons, cycloalkyl having 3 to about 8 carbons, and cyclic structures joining two of $R^1$, $R^2$, $R^3$ and $R^4$ having 3 to about 8 carbon atoms. Representative of alkylene oxides are ethylene oxide; propylene oxide; butylene oxide, including isobutylene oxide; 1,2-butylene oxide and 2,3-butylene oxide; pentylene oxide; styrene oxide; cyclohexene oxide and the like. Preferably, the alkylene oxide is an aliphatic alkylene oxide having 2 or 3 carbon atoms, i.e., ethylene oxide and propylene oxide.

Alkylene oxides are well known, as is their preparation. For example, alkylene oxide can be prepared by reacting an olefin with an organo-hydroperoxide in the presence of a catalyst or by the partial oxidation of an alkene (especially ethylene) with a molecular oxygen-containing gas in the presence of a silver catalyst. Frequently, the alkylene oxide has been purified to avoid the presence of components which may produce troublesome impurities in the alkylene glycol product.

Water is employed as the other reagent for the formation of the corresponding alkylene glycol. Usually the water is of sufficient purity to provide a suitable quality alkylene glycol product. The water may be distilled or demineralized, for example, by ion exchange treatment.

The organometalates may be solid or liquid under reaction conditions. Most often for the sake of convenience, the organometalate is dissolved in a solvent which is liquid under the conditions of the reaction. The liquid solvent should be inert to the organometalate and the alkylene oxide, alkylene glycol and water. The selection of suitable solvents is, in part, based on the ability to dissolve and/or miscibility with the organometalate, and preferably, the alkylene oxide has some degree of solubility in the liquid solvent. Frequently, at least about 5, say, at least about 20 grams of organometalate are soluble per liter in the liquid solvent at 25° C. at atmospheric pressure, and some organometalates will be miscible with the solvent in all proportions under reaction conditions. Exemplary of liquid solvents are alkyl, cycloalkyl and aromatic-containing solvents, especially halogenated alkyl, cycloalkyls and aromatics, such as cyclopentane, cyclohexane, methylcyclohexane, cycloheptane, benzene, toluene, xylene, naphthene, dichloromethane, 1,1,2-trichloroethane, and the like. Silicone oils and mineral oils may also find application. Also, interactive solvents such as 1,2-dimethoxyethane may be used. Not all the above solvents will be suitable for all of the organometalates of this invention.

It is believed that the reaction to alkylene glycol can proceed by at least two routes. The first route is the conventional route in which alkylene oxide is directly reacted with water. Alternatively, alkylene oxide can become associated with the organometalate, which, in turn, when contacted with water, liberates alkylene glycol. When using the organometalates, the selectivity to the monoglycol product can be enhanced as compared to conventional commercial hydrolysis techniques. Alkylene glycols can be produced from alkylene oxides and water in various manners.

One method which is particularly attractive for providing extremely high selectivities to monoalkylene glycol involves sequentially contacting the organometalate with alkylene oxide to form an associated moiety and then contacting the associated moiety with water to form the corresponding alkylene glycol. Such processes, which include, inter alia, organometalates are disclosed in copending U.S. patent application Ser. No. 594,256, filed on even date herewith, of J. R. Briggs, G. L. O'Connor and J. H. Robson. Preferably, the reaction between the alkylene oxide and organometalate is conducted in the presence of little, if any, water to minimize or avoid the formation of alkylene glycols which could react with ethylene oxide to form di- and polyglycols. For example, the mole ratio of water to alkylene oxide initially present may often be less than about 0.5:1, say, less than about 0.1:1, and the reaction medium may be substantially free from water. However, in some instances some water may be provided beneficially to enhance the stability of the metalate anion.

Usually, sufficient organometalate is provided for complete reaction with the alkylene oxide, and an excess of organometalate of the amount required for reaction with alkylene oxide on a stoichiometric basis is employed to ensure a substantially complete conversion. However, lesser amounts of organometalate may be employed if desired. Thus, the mole ratio of organometalate to alkylene oxide is frequently in the range of about 0.1:1 to 50:1, say, about 0.5:1 to 20:1, preferably, about 1:1 to 5:1.

Any unreacted alkylene oxide may be recovered prior to contact with the water or may be passed with the reaction product to contact the water. For the highest selectivity to monoalkylene glycol, it is preferred that the reaction of the alkylene oxide with the organometalate is substantially complete or that the unreacted alkylene oxide is removed prior to contacting water.

The mixture containing the alkylene oxide and organometalate is then contacted with water or steam to form the corresponding alkylene glycol. The water or steam is frequently provided in excess of the amount required to react with the alkylene oxide initially provided; however, lesser amounts can be employed. Thus, the mole ratio of water or steam to total alkylene oxide values may be about 0.5:1 to 50:1, say, about 1. The organometalate-containing phase may be continuously passed through an aqueous phase, or, alternatively, steam or water may be passed through it. Hence, the mole ratio of water or steam to the organometalate and alkylene oxide at a given volume in the reaction menstruum may be greater or lesser than the foregoing mole ratios which are based on the net reactants provided to the reaction zone. When employing steam as the source of water for the liberation of alkylene glycol, little, if any, liquid water will be present to be removed from the alkylene glycol product, e.g., by evaporation. Thus, higher ratios of steam to the vicinal dioxyalkylene organometalate and unreacted alkylene oxide may be advantageous, for instance, about 5:1 to 40:1. On the other hand, when water is employed, it must be removed from the alkylene glycol product, and therefore from the standpoint of energy efficiency, lower ratios of water to total alkylene oxide values are desirable, for instance, about 1:1 to 5:1.

After the reaction with water, the alkylene glycol can then be separated, e.g., by phase separation, from the organometalate-containing phase which may be suitable for reuse in reacting with alkylene oxide. Hence, this mode of operation is particularly convenient for continuous processes in which the organometalate is recycled.

The sequential process may be conducted in any convenient manner. For example, the process may be conducted in two vessels, the first for conducting the reaction between the organometalate and alkylene oxide and the second for the contact with water or steam to yield the alkylene glycol. It is also possible to conduct the process in a single vessel having several zones; in the first portion of the vessel the organometalate and alkylene oxide are contacted and in a later portion water or steam is introduced. The vessels may be provided with means to promote the contact between the reactants. For example, agitators, packing, trays and other devices for promoting liquid-liquid or gas-liquid contact, as the case may be, may be employed. Either phase may be the continuous phase. By way of illustration, steam may be dispersed as fine bubbles throughout a liquid, metalate-containing phase or a liquid, metalate-containing phase may be dispersed in an aqueous phase.

Another illustrative method for producing alkylene glycol involves maintaining a two phase reaction zone wherein the organometalate, alkylene oxide and water are present and these methods, inter alia, are disclosed in copending U.S. patent application Ser. No. 594,385, filed on even date herewith, of J. R. Briggs and J. H. Robson. Since the conventional hydrolysis reaction can occur, various procedures can be employed to enhance the yield of the monoalkylene glycol product. For instance, the alkylene oxide can be introduced into a liquid organometalate-containing phase. Also, large amounts of the organometalate may be provided per unit volume of reactor. Generally, the mole ratio of organometalate to alkylene oxide fed into the reactor is at least about 0.001:1, and is often at least about 0.01:1. In some instances it may be desired to provide the organometalate in an amount greater than that required on a stoichiometric basis for reaction with the alkylene oxide present in the reaction zone. Thus, the mole ratio of organometalate to alkylene oxide may be 5:1 or even 10:1 or greater. Because of the volume of reactor and amount of organometalate required, economics usually dictate that the mole ratio of organometalate to alkylene oxide will be within the range of about 0.1:1 to 2.0:1, say, about 0.5:1 to 1.5:1. With the greater amounts of organometalate chemical kinetics dictate that the relative portion of the alkylene glycol formed through formation of the vicinal dioxyalkylene organometalate is enhanced.

The ratio of water to alkylene oxide may also be relatively low in order to enhance the portion of the alkylene oxide that associates with the organometalate; however, at too low ratios, the concentration of alkylene glycol may be sufficiently high that significant amounts of di- and polyglycols are formed. In general, the ratio of water to alkylene oxide can be lower than that employed for conventional hydrolysis with achieving at least as great a selectivity to monoalkylene glycol. The ratio of water to alkylene oxide is often in the range of about 0.5:1 to 50:1, say, about 1:1 to 20:1, preferably about 3:1 to 10:1 (mole basis).

In the two-phase procedures, the organometalate-containing phase or the aqueous phase may be the continuous phase. Preferably, the discontinuous phase is highly dispersed and is in the form of small bubbles to enhance the interface areas between the phases. Accordingly, devices to enhance the dispersion may be employed such as agitators, spargers, and the like.

In a still further method, the reactions between the organometalate and alkylene oxide and water may be conducted in a homogeneous liquid phase. The organic-containing cation is selected so that the organometalate is preferentially soluble in an immiscible organic liquid such as methylene dichloride, toluene, etc., but yet it is sufficiently soluble in water that selectivity-enhancing amounts of the organometalate can be provided in the reaction menstruum. The effluent from the reaction zone can then be contacted with an immiscible organic solvent to recover the organometalate by extraction. For example, tetra-n-butyl and tetra-n-hexyl ammonium metalate salts exhibit sufficient hygroscopicity that they can be dissolved in large amounts in a water and ethylene oxide-containing reaction medium, and they have sufficient organophilicity, e.g., in toluene, to be extracted using conventional extraction apparatus from the effluent from the reaction zone. Further discussion is provided in U.S. patent application Ser. No. 594,266, now abandoned for Ser. No. 663,827 filed 10-23-85, filed on even date herewith, of B. T. Keen, et al., herein incorporated by reference.

The pH of the reaction menstruum is frequently maintained relatively neutral, e.g., between about 5 and 11, preferably about 6 to 10.5, and most often the pH is in the range of about 6 to 10. With some metalate anions, such as the vanadates, molybdates and tungstates, the pH of the medium can be determinative of the species present. For example, in strong bases orthovanadate may predominate, but at neutral conditions metavanadate will exist. In another example, more acidic media promote the formation of polynuclear molybdates which often have less, if any, activity for enhancing selectivity.

The pH may be maintained within the desired range by the addition of acid or base, or the addition of buffers, as is well known in the art; however, the presence and nature of salts should be considered since the cation may displace the organic-containing cation. Mechanisms which have been proposed for maintaining the desired pH in other types of hydrolysis processes include the addition of carbon dioxide or inorganic acids or organic acids such as sulfuric acid, hydrochloric acid and acetic acid. The agents for maintaining the pH value of the reaction menstruum may be added in any convenient manner such as during the reaction, e.g., by purging with carbon dioxide, or by addition to one or more of the reactants prior to introducing the reactants into the reactor. For example, the pH of the water component may be adjusted to the desired level prior to admixing with the ethylene oxide.

The maintenance of the pH within the desired ranges can also have a secondary effect of enhancing the stability of the organometalate.

The processes may be carried out at temperatures sufficient to enable the reaction between the alkylene oxide and the organometalate. The temperature, however, should not be so great that the organic-containing cation and/or organometalate anion are not unduly adversely affected. Accordingly, the process is often carried out at a temperature between about 20° C. and about 220° C. or 250° C. Most often, the reaction is carried out at a temperature between about 50° C. and 200° C., say, about 80° C. to 180° C.

The processes may be conducted at subatmospheric, atmospheric or superatmospheric pressure. However, often pressures are employed which are sufficient to maintain the organometalate in the liquid phase. For purposes of convenience, the reaction is typically conducted at pressures greater than ambient, e.g., between about 0.1 and 1,000 kilograms per square centimeter gauge and preferably between about 2 and 100 kilograms per square centimeter gauge.

The production of alkylene glycol may be conducted in the presence of a gas, which is preferably inert. Gases which may be employed include air, carbon dioxide, nitrogen, argon and the like. Carbon dioxide is often present during the hydrolysis of alkylene oxide by the very nature of the process and the source of the alkylene oxide (especially by partial oxidation of alkenes). Frequently, it is desired to maintain the mole ratio of carbon dioxide to alkylene oxide less than 0.1:1, particularly less than 0.05:1, unless it is desired to affect the pH of the reaction menstruum. Carbon dioxide can be used in certain amounts to enhance the selectivity provided by vanadate anion such as disclosed in U.S. patent application Ser. No. 594,265, filed on even date herewith, of B. T. Keen, herein incorporated by reference.

Generally, the reaction is conducted for a period of time sufficient to ensure that substantially all the alkylene oxide is reacted. The amount of time required to accomplish the substantially complete reaction is determined by the other conditions employed including temperature, amount of reactants present, and the like. The reaction may be carried out for very short periods of time, e.g., fractions of a second, and, if desired, may be carried out for periods of up to hours, e.g. about 0.01 second to 5 hours, preferably about 1 second to 30 minutes.

The alkylene glycol may be recovered from the reaction effluent in any convenient manner. Typically, the water is removed in a series of multiple-effect evaporators and the alkylene glycol is further refined by vacuum distillation.

The organometalates may also find application in reactions between alkylene oxides and alcohols, e.g., methanol, ethanol, and n-butanol, to form ethers. Reactions with carboxylic acids, amides and the like may also provide useful products.

The following examples are provided to assist in the understanding of the invention and are not in limitation thereof. All percentages and parts of solid are by weight and all percentages and parts of liquids and gases are by volume, unless otherwise indicated.

EXAMPLE 1

A solution of about 5.0 grams of sodium molybdate dihydrate in 20 milliliters of water was prepared in a glass flask. A solution of about 7.0 grams of silver nitrate in 20 milliliters of water was separately prepared in another glass flask and then added to the sodium molybdate-containing solution. A white precipitate immediately appeared. The reaction mixture was stirred for five minutes, and the precipitate was then recovered by filtration. The recovered precipitate was washed with water, then with acetone and finally with diethyl ether. The washed solid was dried in air by suction. The solid (about 7.7 grams) which is silver molybdate, was added to the flask containing a previously prepared solution of about 18 grams of tetra-n-hexylammonium iodide in 75 milliliters of dichloromethane and 5 milliliters of distilled water. The reaction mixture was stirred for about 95 minutes while covered with a paper bag to reduce exposure to light. The insoluble material was filtered and washed several times with dichloromethane. The solvent was removed by stripping under vacuum (about 1 to 2 millibars absolute). The product, bis(tetra-n-hexylammonium)molybdate was identified by infrared spectrographic analysis and was recovered in a yield of 76% (14.0 grams).

EXAMPLE 2

In one glass flask, 4.0 grams of silver nitrate were dissolved in 25 milliliters of water, and, in another, 3.9 grams of sodium tungstate dihydrate were dissolved in 25 milliliters of water. The solutions were combined and stirred for about five minutes. The precipitate was recovered by filtration and washed three times with about 30 milliliters of water, three times with about 30 milliliters of acetone and three times with diethyl ether to recover about 5.4 grams of silver tungstate.

In a further glass flask about 9.37 grams of tetra-n-heptylammonium chloride were dissolved in 125 milliliters of dichloromethane and about 5.37 grams of the silver tungstate were added with 8 milliliters of water. The reaction mixture was stirred for about 6.5 hours while being covered with a paper bag to reduce exposure to light. The silver chloride contained in the reaction medium was removed by filtration using Hi-Flo (TM) filter aid cake on frit. The frit was washed with dichloromethane and added to the remaining liquid. The remaining liquid was stripped under vacuum (about 1 to 2 millibars absolute) to yield about 9.3 grams of product, bis[(tetra-n-heptyl)ammonium]tungstate. The identity of the product was confirmed by infrared spectrographic analysis.

EXAMPLE 3

In a glass flask about 5.11 grams of silver nitrate were dissolved in about 20 milliliters of distilled water. In another glass flask, about 3.64 grams of sodium molybdate were dissolved in about 20 milliliters of distilled water, and the silver nitrate solution was poured into it. The mixture was stirred for about 5 minutes and then filtered at about 10° C. using a 15 milliliter Buchner funnel with frit. The retentate was washed three times with 10 milliliters of distilled water, three times with 10 milliliters of acetone and three times with 10 milliliters of diethyl ether. After sucking dry, the filter cake weighed about 5.64 grams.

A solution of about 15.0 grams of (tetra-n-octadecyl)ammonium bromide in 62.5 milliliters of dichloromethane was prepared in a glass flask by heating. Then, while stirring at 30° C., the previously prepared filter cake was introduced into the solution. After six hours, the solution was heated to reflux (at ambient pressure). The solution was filtered, and the filtrate was stripped of volatiles under vacuum (about 1 to 2 millibars absolute). About 15.01 grams of bis(tetra-n-octadecyl)ammonium molybdate were recovered and its identity was confirmed by infrared spectrographic analysis.

EXAMPLE 4

Into a glass flask containing at about 50° C. a previously prepared solution of about 1 gram of silver nitrate in 3 milliliters of distilled water was added a solution of about 0.72 grams of sodium metavanadate in 30 milliliters of distilled water which was at a temperature of about 60° C. The admixture was stirred for about 10 minutes while the temperature remained at about 50° C. to 60° C. An orange-yellow precipitate formed and was recovered by filtration. The solid was washed three times with distilled water, three times with acetone and three times with diethyl ether then dried in air under suction.

In another glass flask, a solution of 2.55 grams of (tetra-n-hexyl)ammonium iodide in 30 milliliters of dichloromethane was prepared. About 3 milliliters of water were added and then, while stirring at ambient temperature, the previously prepared silver vanadate was added. The stirring continued for about 1.5 hours while under a paper bag to reduce the exposure to light. The precipitate changed color from an orange-yellow appearance to pale yellow during the course of the process. The precipitate was recovered by filtration and washed thoroughly with dichloromethane using Hi-Flo (TM) filter aid and the wash liquid was added to the filtrate. The filtrate was then stripped under vacuum (about 1 to 2 millibars absolute). The identity of the product, (tetra-n-hexyl)ammonium vanadate, was confirmed by infrared spectrographic analysis.

EXAMPLE 5

In a glass flask, a previously prepared solution of about 1.2 grams of tetra-n-propylammonium iodide in 25 milliliters of water was added to 1.2 grams of silver molybdate while stirring at ambient temperature (i.e., about 20° to 25° C.). After about 15 minutes, the insoluble material was removed by filtration. The remaining, colorless solution was stripped of volatiles at a temperature not exceeding 30° C. under vacuum (about 1 to 2 millibars absolute). The recovered liquid was washed with diethyl ether, dried under vacuum (about 1 to 2 millibars absolute) at 50° C. and cooled to −78° C. to crystallize the product. The product remained crystalline when warmed to room temperature. The product, bis(tetra-n-propyl ammonium) molybdate, was obtained in the amount of about 0.96 grams and, because of its hygroscopic nature, was maintained in a desiccator. The identity of the product was confirmed by infrared spectrographic analysis.

The following Table exemplifies further reactants and products.

TABLE

| Example | Organic-Containing Cation | Heavy Metal Metalate | Mole Ratio of Organic-Containing Cation to Metalate Anion |
|---|---|---|---|
| 6 | bis(triphenylphosphine)iminium | silver tungstate | 1.9:1 |
| 7 | bis(triphenylphosphine)iminium | silver tungstate | 0.8:1 |
| 8 | tetradodecylammonium chloride | silver metavanadate | 0.99:1 |
| 9 | tetrahexylphosphonium bromide | silver molybdate | 1.9:1 |
| 10 | octadecylammonium chloride | silver molybdate | 0.3:1 |
| 11 | tetra-n-hexylammonium sulfate | barium molybdate | 0.2:1 |
| 12 | tetra-n-heptylammonium sulfate | calcium tungstate | 0.1:1 |

| Example | Temperature, °C. | Solvent | Organometalate Product |
|---|---|---|---|
| 6 | 10° C. | toluene | bis[bis(triphenylphosphine)iminium]tungstate |
| 7 | 20° C. | dichloromethane | mixture of bis(triphenylphosphine)iminium tungstate and bis[bis(triphenylphosphine)iminium]tungstate |
| 8 | 20° C. | 1,1,2-trichloroethane | tetradodecylammonium vanadate |
| 9 | 35° C. | dichloromethane | bis(tetrahexylphosphonium)molybdate |
| 10 | 30° C. | benzene | bis(octadecylammonium)molybdate |
| 11 | 5° C. | dichloromethane | bis(tetra-n-hexylammonium)molybdate |
| 12 | 5° C. | toluene | bis(tetra-n-heptylammonium)tungstate |

It is claimed:

1. A process for the preparation of an organometalate having at least one organic-containing cation and metalate anion of the structure $$[(A)_qM(O)]^{a-}$$

wherein M is a polyvalent metal having a functional positive oxidation state, A represents one or more substituents to fill the remaining valencies (q) of M, and a— is the negative charge of the anion, comprising dissolving in a solvent-containing reaction menstruum a soluble salt containing the organic-containing cation; and contacting said soluble salt with a heavy metal salt of said metalate anion to produce the organometalate, said solvent being a solvent for the organometalate under the conditions during the contact, and to co-produce a salt of the heavy metal cation and the anion provided by the salt having the organic-containing cation, said salt of the heavy metal cation being substantially insoluble in the reaction menstruum under the conditions during the contact.

2. The process of claim 1 wherein the heavy metal cation comprises silver.

3. The process of claim 2 wherein the metalate anion is at least one member selected from the group consisting of tungstate, molybdate and vanadate.

4. The process of claim 3 wherein the organic-containing cation comprises an organoammonium or an organophosphonium cation having at least one substituent having at least 4 carbon atoms.

5. The process of claim 1 wherein the reaction menstruum comprises organic solvent.

6. The process of claim 2 wherein the anion for the soluble salt of the organic-containing anion is a halide.

7. The process of claim 1 wherein the heavy metal metalate is substantially insoluble in the reaction menstruum.

8. A process for making an organometalate of the formula:

$$[(R^0)_mY_n]^{x'+}[L^{x+}]_{z-1}[(A)_qM(O)]^{a-}$$

wherein Y is a polyvalent element which is an ionic charge carrying center; $R^0$ is hydrogen or hydrocarbyl-containing substituent with the proviso that Y has at least one $R^0$ which contains a hydrocarbyl substituent; m is the average number of electron pairs shared by each Y with the total $R^0$ groups; n is the number of charge carrying centers, wherein m, n and x are related by the equation $x = n(v-m)$ in which V is the average functional oxidation state of Y wherein each electron pair used by each Y in bonding to R(0) is given the value of 1 and the formal oxidation state of Y is the sum of the electron pairs bonding to $R^0$ and x/n, wherein x is an integer of 1 or 2; L is a cation which has a positive charge of x' wherein x' is 1 or 2 and L is selected from the group consisting of

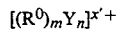
$$[(R^0)_m Y_n]^{x'+}$$

alkaline metal, quaternary ammonium and quaternary phosphonium cations; z is 1 to 3; M is a polyvalent metal having a functional positive oxidation state; A represents one or more substituents to fill the remaining valencies (q) of M and is selected from the group consisting of double bonded oxygen, and —O—, comprising dissolving in a solvent-containing reaction menstruum a soluble salt of $[R^0{}_m Y_n]^{x'+}$; and contacting said soluble salt with a heavy metal salt of $[(A)_q M(O)]^{a-}$ to produce the organometalate, said solvent being a solvent for the organometalate under the conditions during the contact and to produce a salt of the heavy metal cation and the anion to the soluble salt of $[R^0{}_m Y_n]^{x'+}$, said salt being substantially insoluble in the reaction menstruum under the conditions during the contact.

9. The process of claim 8 wherein M is molybdenum, vanadium or tungsten.

10. The process of claim 8 wherein Y is nitrogen or phosphorous and each $R^0$ is hydrocarbyl-containing.

11. The process of claim 10 in which at least one $R^0$ has at least four carbon atoms.

12. The process of claim 8 in which sufficient carbons are provided in at least one $R^0$ substituent that the organometalate is soluble in an organic solvent.

13. The process of claim 8 in which sufficient carbons are provided in at least one $R^0$ substituent that the organometalate is substantially insoluble in water.

14. The process of claim 8 wherein $[R^0{}_m Y_n]^{x'-}$ is a quaternary ammonium.

15. The process of claim 14 wherein each substituent of the quaternary ammonium has about 4 to 20 carbon atoms.

16. The process of claim 8 wherein the heavy metal cation is silver cation.

17. The process of claim 16 wherein the anion of $[R^0{}_m Y_n]^{x'+}$ is a halide.

18. The process of claim 16 wherein $[(A)_q M(O)]^{a-}$ is tungstate, molybdate or vanadate.

19. The process of claim 18 wherein the heavy metal salt of $[(A)_q M(O)]^{a-}$ is substantially insoluble in the reaction menstruum under the conditions during the contact.

20. The process of claim 8 wherein the organometalate-containing reaction menstruum is separated from insoluble heavy metal salt.

21. The process of claim 20 wherein organometalate is recovered from the separated reaction menstruum.

22. The process of claim 19 wherein the reaction menstruum comprises organic solvent.

23. The process of claim 8 wherein the contacting is conducted at a temperature of 10° C. to 70° C.

24. A process for the preparation of an organometalate having at least one organic-containing cation and metalate anion comprising dissolving in a solvent-containing reaction menstruum, a soluble salt containing the organic-containing cation; and contacting said soluble salt with a heavy metal salt of said metalate anion to produce the organometalate, said solvent being a solvent for the organometalate under the conditions during the contact, and to produce a salt of the heavy metal cation and the anion provided by the salt having the organic-containing cation said salt of the heavy metal cation being substantially insoluble in the reaction menstruum under the conditions during the contact.

25. The process of claim 24 wherein the salt of the heavy metal cation is substantially a solid in the reaction menstruum under the conditions during the contact.

26. The process of claim 25 wherein the heavy metal cation comprises silver.

27. The process of claim 26 wherein the metalate anion is at least one member selected from the group consisting of tungstate, molybdate and vanadate.

28. The process of claim 27 wherein the organic-containing cation is an organoammonium or an organophosphonium cation having at least one substituent having at least 4 carbon atoms.

29. The process of claim 28 wherein the heavy metal metalate is substantially insoluble in the reaction menstruum.

30. The process of claim 29 wherein the reaction menstruum comprises organic solvent.

* * * * *